United States Patent [19]
Ansari et al.

[11] Patent Number: 5,973,779
[45] Date of Patent: Oct. 26, 1999

[54] FIBER-OPTIC IMAGING PROBE

[76] Inventors: Rafat R. Ansari, 3949 Silsby Rd., University Heights, Ohio 44118-3138; Kwang I. Suh, 17 Normandy Dr., Jackson, N.J. 08527

[21] Appl. No.: 08/828,371

[22] Filed: Mar. 28, 1997

Related U.S. Application Data

[60] Provisional application No. 60/014,438, Mar. 29, 1996.

[51] Int. Cl.$^6$ ............... G01N 21/49; G01N 21/64; G01N 21/65
[52] U.S. Cl. ............... 356/301; 356/318; 356/342
[58] Field of Search ............... 356/301, 336, 356/338, 342, 317, 318; 250/458.1, 461.1

[56] References Cited

U.S. PATENT DOCUMENTS

| | | |
|---|---|---|
| 4,762,413 | 8/1988 | Namba et al. . |
| 4,776,687 | 10/1988 | Nakanishi et al. . |
| 4,836,207 | 6/1989 | Brusell et al. . |
| 4,854,693 | 8/1989 | Ichihashi et al. . |
| 4,957,113 | 9/1990 | Benedek . |
| 4,975,237 | 12/1990 | Brown . |
| 4,983,040 | 1/1991 | Chu et al. . |
| 4,993,827 | 2/1991 | Benedek et al. . |
| 5,155,549 | 10/1992 | Dhadwal . |
| 5,284,149 | 2/1994 | Dhadwal et al. . |

FOREIGN PATENT DOCUMENTS

| | | |
|---|---|---|
| 0 106 684 | 4/1984 | European Pat. Off. . |
| 2122034 | 8/1972 | France . |
| 61-155839 | 7/1986 | Japan . |

OTHER PUBLICATIONS

Auweter et al., "Fiber–Optical Quasi–elastic Light Scattering of Concentrated Dispersions," Journal of Colloid and Interface Science, vol. 105, No. 2 (Jun. 1985).

Tanaka et al., "Measurement of the Velocity of Blood Flow (in vivo) Using a Fiber Optic Catheter and Optical Mixing Spectroscopy", Appl. Opt., vol. 14, pp. 189–196, 1975.

Macfadyen, "Fiber Optic Systems for Dynamic Light Scattering—a Review", Optics and Laser Technology, vol. 22, pp. 175–187, 1990.

Ricka, "Dynamic Light Scattering with Single–Mode and Mutimode Receivers", Appl. Opt., vol. 32, pp. 2860–2875, 1993.

Brown, "Optical Fiber Sensing Using Light Scattering Techniques", J. Phys. E: Sci. Instrum., vol. 20, pp. 1312–1320, 1987.

Dhawal et al., "Fiber–Optic Light–Scattering Spectrometer", Rev. Sci. Instrum., vol. 60, pp. 845–853, 1989.

Wiese et al., "Single–Mode Fibers in Fiber–Optic Probe for Particle Sizing in Concentrated Suspensions", Rev. Sci. Instrum., vol. 62, pp. 2963–2968, 1991.

Dhadwal et al., "A Fiber–Optic Probe for Particle Sizing in Concentrated Suspensions", Rev. Sci. Instrum., vol. 62, pp. 2963–2968, 1991.

Rovatti et al., "Dynamic Light Scattering Spectroscopy of in–vivo Human Vitreous", Proc. SPIE, vol. 2632, pp. 73–78, 1995.

Primary Examiner—F. L. Evans
Attorney, Agent, or Firm—Fay, Sharpe, Beall, Fagan, Minnich & McKee, LLP

[57] ABSTRACT

A fiber-optic imaging probe is disclosed for use in dynamic light scattering applications. The probe includes two monomode optical fibers and two GRIN lenses to form a pair of identical fiber-lens combinations. Each fiber is positioned off the optical axis of its associated lens. Further, the optical fibers are placed at an image plane of the lenses. The fiber-lens combinations are parallel to and mirror images of each other. The first fiber-lens combination projects a tightly focused spot of light into a scattering volume containing suspended or dispersed microscopic particles, or biological or live tissues. The second fiber-lens combination collects the light which is scattered from the particles in the scattering volume and conveys it to a photo detector and autocorrelator for analysis. The probe minimizes the scattering volume by advantageously using imaging principles of lenses. Further, the probe optimizes sensitivity and spatial coherence. The probe provides rapid determination of particle diffusivities and their respective size distributions in the scattering volume. The probe can be combined with a video and/or microscopic imaging system for visual monitoring of the scattering volume in real time. The probe may be used in a wide variety of optical diagnostic applications. Further, the probe is easy to manufacture and use.

29 Claims, 12 Drawing Sheets

FIBER-OPTIC IMAGING PROBE

This application claims the benefit of Provisional Application No. 60/014,438, filed on Mar. 29, 1996.

BACKGROUND OF THE INVENTION

This invention pertains to the field of dynamic light scattering which is also known as quasi-elastic light scattering (QELS), intensity fluctuation spectroscopy (IFS), optical mixing spectroscopy, and photon correlation spectroscopy (PCS). More particularly, this invention pertains to the characterization of particle suspensions or dispersions using DLS. The invention is applicable to eye diagnostics such as the diagnosis of eye diseases (cholesterol deposit and blood sugar level in the anterior chamber, cataract in the lenses, diabetic retinopathy, age related molecular change in the vitreous, etc.) and will be described with reference thereto. However, it will be appreciated that the invention has broader applications such as monitoring the synthesis of microporous materials (e.g., zeolite), monitoring protein crystallization process, characterization of food proteins, analyzing skin and tissue, diagnosing biological fluids in situ and in vivo, on-line process monitoring, studying polymer induced aggregation and flocculation, studying highly concentrated and interacting systems, and characterizing diverse systems such as gels, solids, liquid crystals, colloidal suspensions, polyelectrolyte solutions, dispersions of microorganisms and solutions of viruses and biopolymers. Moreover, the invention may be advantageously employed in other environments and applications including static light scattering, Brillouin scattering, Raman scattering, fluorescence spectroscopy and laser doppler velocimetry and anemometry.

DLS is a widely used technique in studying the hydrodynamic properties of microscopic particles suspended in a fluid medium. Some of the information that can be obtained from DLS include the diffusion coefficient, average particle size, polydispersity, and particle size distribution.

The concept of DLS has been in use for the last half century, and numerous publications and books have been published on the subject. For example, the basic theory and experimental aspect of DLS can be reviewed in the book by Chu [*Laser Light Scattering: Basic Principles and Practice*, 1991].

In DLS, coherent light such as laser light illuminates microscopic particles dispersed or suspended in a fluid medium. The particles range in size from a few nanometers to a few microns. The particles scatter light over a wide range of angles by Rayleigh or Mie scattering. The intensity of the scattered light fluctuates in time due to the Brownian or thermal motion of the particles in the medium. The fluctuations of the light intensity contain information about the dynamics of the scattering particles. This information can be extracted by constructing a time correlation function (TCF). The TCF is computed using a digital correlator. In the case of dilute dispersions of spherical particles, the TCF provides quick and accurate determination of the translation diffusion coefficient of the particles. Using the Stokes-Einstein equation, the diffusion coefficient can easily be transformed into average particle size provided the viscosity of the suspending medium, its temperature, and refractive index are known.

A conventional apparatus for DLS experiments includes a source of laser light and a transmitting optical arrangement to launch the laser light into an illumination volume of a sample. The apparatus also includes a collecting optical arrangement to coherently collect the scattered laser light from a detection volume in the sample. The overlap of the illumination volume and the detection volume is the scattering volume.

A major problem in DLS systems is optical alignment. The optical arrangements must b e precisely aligned to obtain meaningful data. This is a tedious procedure that unfortunately limits the use of DLS to well-controlled environments such as a laboratory.

The recent use of fiber optics in DLS systems partially addresses the problem of optical alignment. First initiated by Tanaka and Benedek [*Appl. Opt.*, 14, 189 (1975)], fiber optics provide several advantages over conventional optics in DLS systems. Fiber optics are compact, rugged, easy to handle, and portable.

The problem of optical alignment has also been partially re solved by integrating the transmitting and collecting optical arrangements into a single compact housing. This has allowed DLS to be used in areas such as biomedical diagnostics, remote sensing, and on-line process control. For example, Tahaka and Benedek showed that a compact fiber optic probe can be used to measure the velocity of the blood flow inside the human body. Other examples of fiber optic based DLS systems have been reviewed by Macfadyen [*Optics and Laser Technology*, 22, 175 (1990)].

In designing a DLS system, there are primarily two parameters that must be optimized: sensitivity and spatial coherence. Sensitivity is an indication of how high the scattered intensity would be with a given input laser power. Spatial coherence or signal to noise ratio is an indication of how much of the scattered light contains usable signal. Generally, optimizing one parameter can only be done at the expense of the other parameter. In other words, increased sensitivity can only be achieved by lowering spatial coherence, and vice versa. This relationship occurs because both parameters are controlled by the size of the scattering volume. The larger the scattering volume, the greater the intensity of collected light. However, the larger the scattering volume, the lower the spatial coherence. Therefore, a major design objective in DLS systems is an optimal balance between sensitivity and spatial coherence.

Some DLS systems use monomode optical fibers to transmit light through the system. Such systems can be separated into two groups—lensless probe designs and collimating probe designs. Lensless probe designs do not use lenses to transmit or receive laser light. Consequently, the beams from such systems are divergent. Collimating probe designs, on the other hand, use lenses to produce collimated beams of laser light in the scattering volume.

Lensless probe designs are exclusively used in the backscattering regime. Typically, they consist of a single fiber for transmission and reception of the laser light. Such designs suffer from a very small penetration depth (on the order of a few $\mu m$) which is the distance between the probe, specifically the end face of the optical fiber, and the center of the scattering volume. This largely limits its application to the examination of immersible fluids wherein the probe is immersed in the fluid sample to obtain measurements.

Another problem with lensless designs is the heterodyning effect due to the internal reflection at the tip of the fiber. This necessitates a great deal of care in fabrication, and limits its application to scattering volumes containing high concentrations of suspended particles so that the scattered signal is strong enough to overcome the reflected signal.

In a two-fiber lensless probe, two monomode fibers are fixed to a housing to achieve a narrow angle between incident and back-scattered laser light. This increases the penetration depth although the depth is still only on the order of a few millimeters. The lensless probe suffers from low sensitivity and low spatial coherence. As a result, the probe is effective for only a limited range of particle sizes and concentrations. When using the probe with a low-power laser, such as in in vivo diagnostics, the range is still further limited. At greater penetration depths, the lensless probe has even lower sensitivity and spatial coherence.

In collimating probe designs, optical fibers are mated with lenses to produce collimated beams of laser light. In such designs, an end face of a monomode optical fiber is positioned at the Fourier plane (also called focal plane) of the lens to produce a collimated illumination volume. This approach, however, significantly compromises the sensitivity and spatial coherence of the probe.

There are essentially two types of optical fibers commercially available for use in DLS systems. One is multimode fiber and the other is monomode fiber or single-mode fiber. There is also polarization-maintaining fiber but it is generally considered to be a subclass of monomode fiber. All of the early fiber-optic DLS systems use multimode fibers because laser light couples more easily with a multi-mode fiber than with a monomode fiber. Further, until recently, no theoretical study showed any advantage of monomode fiber over multimode fiber in DLS systems. Indeed, multimode fiber collects much more scattered light than monomode fiber. However, multimode fiber has very poor spatial coherence. Thus, additional pinholes or apertures are needed in the optical arrangements to enhance the spatial coherence to an acceptable level.

The use of monomode optical fiber was first explored in Brown, *J. Phys. E: Sci. Instrum.*, 20, 1312 (1987). Brown designed a 90° DLS system using monomode optical fiber and micro lens. An advantage of monomode fiber is that it uniquely transmits only a single, spatially-coherent mode of light. This effectively eliminates the need for pinholes or apertures, as was pointed out by Ricka [*Appl. Opt.*, 32, 2860 (1993)] in his theoretical study of monomode fiber.

Later, a multiangle DLS spectrometer system using monomode optical fiber and a graded index (GRIN) lens was taught in Dhadwal and Chu, *Rev. Sci. Instrum.*, 60, 845 (1989)]. In both Brown, and Dhadwal and Chu, the end face of the monomode fiber is placed at the focal plane, also known as the Fourier plane, of the lens. This results in a well-collimated beam and hence well-collimated scattering volume. According to Brown, this configuration yields maximum spatial coherence. See Brown, U.S. Pat. No. 4,975,237 (using monomode optical fiber) Dhadwal and Chu, on the other hand, emphasize higher scattered intensity at the expense of spatial coherence to provide accurate results. See Chu and Dhadwal, U.S. Pat. No. 4,983,040; and Dhadwal, U.S. Pat. No. 5,155,549. Further, they teach that in some cases, using multimode fiber instead of monomode fiber produces better results.

Wiese and Horn [*J. Chem. Phys.*, 94, 6429 (1991)] teach another backscattering DLS system using a lensless backscattering probe having a monomode optical fiber and a directional coupler. This configuration is reported to work well in studying high concentration samples in which the scattering volume is placed at the tip of the fiber. Dhadwal et al. [*Rev. Sci. Instrum.*, 62, 2963 (1991)]I disclose yet another system using two monomode fibers in a lensless. In these lensless designs, the laser beam launched from the monomode fiber diverges with the numerical aperture of the fiber. This produces an overly large, relatively uncollimated illumination volume. Analogously, the lensless collecting optical arrangement produces an overly large and relatively uncollimated detection volume. The results in an overly large scattering volume.

There are several patents on DLS systems using monomode optical fibers. U.S. Pat. No. 4,975,237 to Brown teaches a DLS system in which an end face of a monomode optical fiber is positioned at the focal plane of a lens. This arrangement uses the Fourier transforming property of the lens. The same Fourier transforming principle is also taught in U.S. Pat. No. 4,983,040 to Chu and Dhadwal in a multiangle spectrometer and in U.S. Pat. No. 5,155,549 to Dhadwal in a backscattering probe. In both patents, the scattering volume is created by crossing two beams or volumes that are collimated.

U.S. Pat. No. 5,155,549 to Dhadwal and U.S. Pat. No. 5,284,149 to Dhadwal and Ansari disclose backscattering DLS probes having monomode optical fibers and no lenses. The fibers create diverging illumination and detection volumes. By angling the end portions of the fibers inward, the resulting scattering volume is somewhat minimized.

In the field of eye diagnostics (e.g., cataractogenesis, uvetis, and diabetic retinopathy) devices using DLS have elaborate instrumentation and bulk optics. Such DLS devices have optical alignment problems, statistical errors in data analysis, high patient radiation exposure and multiple scattering problems associated with mild and severe cataracts and the polydisperse nature of the cataract itself.

Lensless backscatter fiber-optic probes have been used to study cataractogenesis in eye lenses. However, for reasons stated above, the probe must be brought into close and uncomfortable proximity to the corneal surface of the eye. Moreover, it is very difficult to accurately pinpoint a desired location in the eye. This is because both the effective depth of the scattering volume and the maximum thickness of an adult human lens are about 0.5 mm. Further, the expanding incident laser light tends to disadvantageously illuminate the entire lens. Still further, when the probe is moved beyond about 2.5 mm from the eye/air border, backreflection starts to cause a significant amount of distortion in the collected scattered light. This backreflection increases the photon count rate in the detector and reduces the spatial coherence values. Because of these limitations, in-vivo measurements can only be performed in the front part (anterior cortex) of the eye lens. The nucleus of the eye lens, the posterior cortex, and the vitreous body cannot be probed or accessed reliably by the lens-less probe.

Therefore, it has been deemed desirable to develop a DLS system that has high sensitivity and high spatial coherence. Further, it is has been deemed desirable to develop a DLS system that is accurate, compact, easy to manufacture and easy to use.

The present invention contemplates a new and improved laser light scattering apparatus and method that overcomes all of the above noted problems and others and provides integrated transmitting and receiving optical arrangements for accurate characterization of particles size and related information and is simple and economical to manufacture and use.

SUMMARY OF THE INVENTION

In accordance with one aspect of the present invention, a dynamic light scattering apparatus for analyzing a scattering volume comprises a probe body. Further the apparatus comprises a transmitting optical arrangement for transmitting coherent light to a scattering volume. The first optical arrangement has a transmitting optical fiber. The transmitting optical fiber has a first optical fiber end face at a first end portion and a second optical fiber end face. The first optical fiber end face is secured to the probe body. The apparatus further comprises a receiving optical arrangement for receiving light from a scattering volume. The second optical arrangement has a receiving optical fiber. The receiving optical fiber has a first optical fiber end face at a first end portion and a second optical fiber end face. The first optical fiber end face of the receiving optical arrangement is secured to the probe body.

In accordance with a more limited aspect of the invention, the apparatus further comprises a transmitting lens located a first selected distance from the first optical fiber end face of the transmitting optical arrangement to minimize the scattering volume.

A principle advantage of the invention is the accurate determination of particle sizes over a wide range of particle sizes and over a wide range of concentrations. A further advantage is that this determination is done in a relatively short period of time. Also, the fiber-optic imaging probe of the present invention offers superior sensitivity and spatial coherence. A further advantage is the integration of transmission and reception systems effectively eliminating the problem of misalignment. A further advantage is that the invention permits the use of low laser power which is more suitable to in vivo testing.

Still a further advantage is a probe which has increased penetration depth to target different areas of a scattering volume. In studies of eyes, this permits investigation of the anterior chamber, the lens, and the posterior chamber of the eye without touching any part of the eye.

Still a further advantage of the invention resides in the use of monomode fiber which selects and propagates only a fully spatially coherent single optical mode providing high spatial coherence.

A further advantage of the present invention is a monomode fiber-optic back-scattering DLS probe that minimizes the scattering volume given parameters of scattering angle, penetration depth, and the focal length of the lens.

A further advantage of the present invention is an optical diagnostic system using any of DLS, static light scattering, Brillouin Scattering, Raman scattering, Laser Doppler velocimetry, and fluorescence spectroscopy.

Yet another advantage of the present invention is that it easily incorporates video monitoring devices.

Still other advantages and benefits of the invention will become apparent to those skilled in the art upon a reading and understanding of the following detailed description.

BRIEF DESCRIPTION OF THE DRAWINGS

The invention may take physical form in certain parts and arrangements of parts, a preferred embodiment of which will be described in detail in this specification and illustrated in the accompanying drawings which form a part hereof, and wherein.

DETAILED DESCRIPTION OF THE PREFERRED EMBODIMENT

Figure 1:
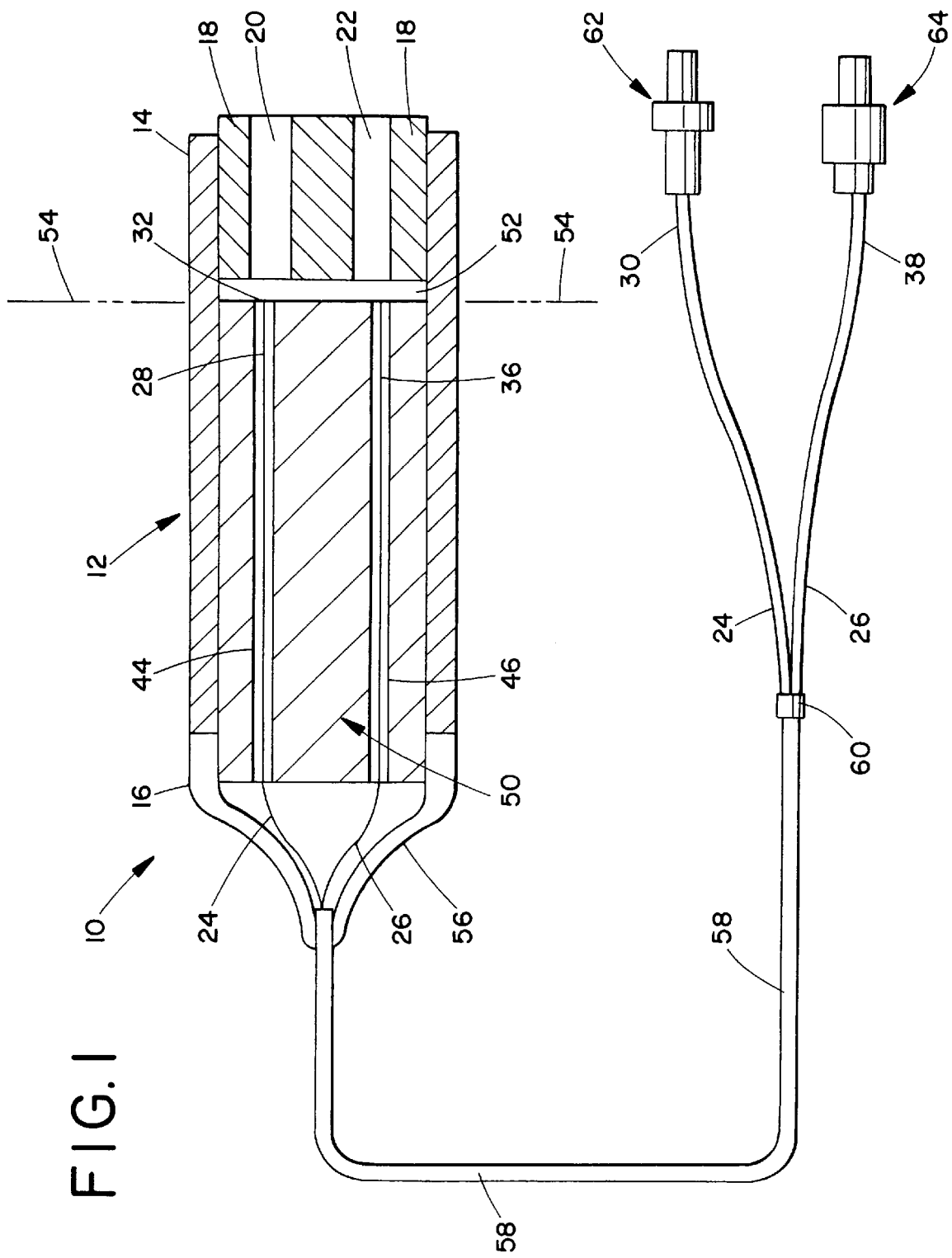
FIG. 1 is a cross-sectional view of a preferred embodiment of the fiber-optic imaging probe of the present invention.

Referring now to the drawings wherein the showings are for purposes of illustrating the preferred embodiment of the invention only and not for purposes of limiting same, FIG. 1 shows a preferred embodiment of the invention of a compact backscatter fiber-optic imaging probe 10 which combines light transmitting optical arrangements and light receiving optical arrangements into a single compact probe body 12.

The probe body 12 has a front end 14 and a back end 16. At the front end 14 is a lens housing 18 in which a pair of quarter pitch, graded index (GRIN) microlenses 20, 22 are seated. The first or transmitting lens 20 is adapted to transmit laser light while the second or receiving lens 22 is adapted to receive scattered laser light.

The preferred embodiment uses quarter pitch GRIN microlenses. GRIN lenses are small in size and easy to incorporate into the lens housing due to their cylindrical shape. Quarter pitch GRIN microlenses have advantageous optical properties in the preferred embodiment. However, the probe can be fabricated using other pitches and other commercially available lenses such as thin lenses.

Seated behind the GRIN lenses 20, 22 are a transmitting optical fiber 24 and a receiving optical fiber 26. The transmitting optical fiber 24 has a first end portion 28 and second end portion 30, and a first end face 32 and a second end face 34 (not visible in FIG. 1). Similarly, the receiving optical fiber 26 has a first end portion 36 and second end portion 38, and a first end face 40 and a second end face 42 (not visible in FIG. 1). The first end portions 28, 36 of the optical fibers are each threaded through ferrules 44, 46 which are seated in fiber housing 50. The first ends 28, 36 of the optical fibers are seated in a position off the optical axis of their respective GRIN lenses 20, 22.

The probe body 12, the lens housing 14, the ferrules 44, 46 and the fiber housing 50 are preferably manufactured of stainless steel. However, it will be appreciated that other materials may be used without departing from the scope of the invention.

The fiber housing 50 and the lens housing 18 are positioned to leave an air gap 52 therebetween. The length of the air gap is designed to place the first end faces 32, 40 of the optical fibers 24, 26 at an image plane 54 of the respectively associated GRIN lenses 20, 22. The scattering volume is thus located at the object plane of both GRIN lenses. The distance between the lens housing and the scattering volume is the penetration depth. The gap, as well as the off-axis configuration of the fiber lens combinations, permits the optical arrangements, i.e., the fibers, the lenses and the air gap, to produce a tightly focussed scattering volume at a desired penetration depth in the sample. The length of the gap 52 is set according the desired penetration depth. The relationship among the distance of the end faces from the lenses can be determined using known lens equations for GRIN lenses; however, for the preferred embodiment, the relationship is visually determined using a beam measuring instrument. It is understood by one skilled in the art that the air gap also depends on pitch or focal length of the lenses.

Heat-shrink tubing 56 encloses the back end 16 of the probe body 12. Flexible tubing 58 surrounds the optical fibers 24, 26 between the first ends 28, 36 and the second ends 30, 38. At the junction of the flexible tubing 58 and the seconds ends 30, 38 of the optical fibers is a small section of Teflon tubing 60. The two second end portions 30, 38 of the optical fibers 24, 26 are terminated with FC/PC-type male connectors 62, 64 for easy mating with a laser/detector module (shown in FIG. 2).

The probe parts are precision machined with strong emphasis on minimizing the tolerances. During the assembly process, laser beams are launched out of the first end portions of the optical fibers. The overlap of the light beams from the fibers defines the scattering volume. The fibers are positioned adjacent the GRIN lenses such that the beams out of the probe overlap each other at the object plane. Each end portion of the optical fibers produces minimum beam waists at the scattering volume or object plane. The assembly process involves a continuous monitoring of the diameters and relative positions of the beams at the object plane using a beam measuring instrument while the position of the fibers are optimally adjusted. The components are bonded together with fast curing epoxy to prevent any movement thereof.

The probe creates a small scattering volume using two tightly focused beams. The tightly focused beams result from the arrangement of the fibers and lenses. It should be noted that none of the end faces of the fibers or the lenses face directly towards the scattering volume. In fact, the fiber-lens combinations are positioned parallel to each other such that end portions of the fibers and the lenses are angled from the scattering volume. This minimizes misalignment that may be caused by manufacturing tolerances of the probe parts. Further, the parallel arrangement of the fibers and lenses minimizes the size of the probe body.

The probe optimizes both sensitivity and spatial coherence. Sensitivity is not only dependent on the size of the scattering volume from which the scattered light is collected, but it is also dependent on the power density of the light in the scattering volume. Increasing the power density increases the sensitivity. This is achieved in the present invention by reducing the illumination beam size at the scattering volume, i.e., by tightly focusing the input beam at the scattering volume. Thus, high sensitivity is achieved without loss of spatial coherence. At the same time, spatial coherence is optimized without the constraint imposed by lower sensitivity and therefore, the scattering volume from which the detector collects the scattered light can be made as small as possible.

Figure 2:
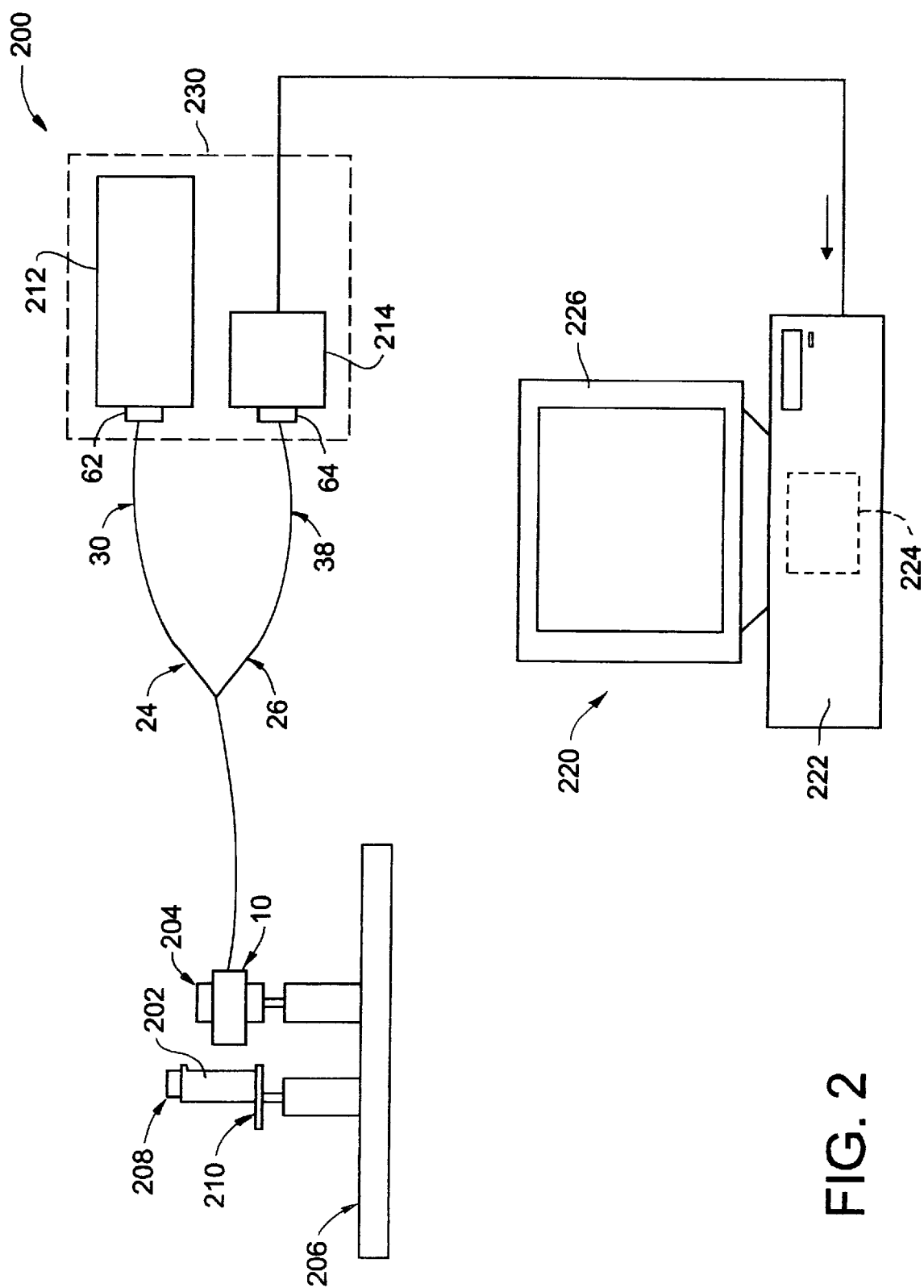
FIG. 2 is a diagrammatic illustration of a preferred DLS system of the present invention.

Referring to FIG. 2, a DLS system 200 incorporating probe 10 analyzes a sample 202. The probe is held by probe holder 204 which is mounted on base 206. The sample is contained in cuvette or sample container 208 which is held by sample holder 210. The sample holder is also mounted to the base. The probe holder holds the probe a certain distance from the sample to examine a desired depth in the sample. The FC/PC-type male connectors 62, 64 connect the two second end portions 30, 38 of the optical fibers 24, 26 to a laser 212 and a photodiode or detector 214, respectively. The laser launches laser light into transmitting optical fiber 24, through the probe and into the sample. Scattered laser light is received by the probe and carried along receiving optical fiber 26 to the detector where it is amplified, discriminated, and converted into TTL logic pulses. A data acquisition system 220 comprising a computer 222 and digital correlator 224 receives the signal from the detector and processes to determine the characteristics of the suspended particles. The computer contains certain data such as the viscosity of the suspending medium, its temperature, and refractive index. Using a correlator software package, the computer processes the TCF and the certain data to obtain average particle size and particle size distribution. Of course, the computer may generate any one or more of particle size, particle size distribution, viscosity of the fluid medium, temperature of the fluid medium or refractive index of the fluid medium provided some or all of the other factors are known. Similarly, other data may also be obtained using the invention. This information may be conveniently stored on the data acquisition system and compared with data collected earlier to identify any changes in the characteristics of the sample. The data is displayed on video monitor 226.

Although FIG. 2 shows a desktop computer, a laptop or other small computer may be used to make the DLS system more portable. For increased portability and decreased set up time, the laser and detector and digital correlator may be combined into one unit exemplified by module 230.

More particularly, the DLS system of the preferred embodiment has a probe with a scattering angle of 154° and a penetration depth of 4.5 mm, both in water. The probe body is 0.5 inches in diameter and less than 1 inch in length. Each monomode fiber is 2 m long. Surrounding the fiber is a protective buffer or cover that is 0.9 mm thick. The illumination laser is a He—Ne laser (Melles Griot Model 05LHP991). As discussed below, the He—Ne laser is also used during manufacture of the probe. The measured beam diameter at the scattering volume is 20 $\mu$m. The probe is tested using polystyrene samples with various particle sizes (32 nm to 800 nm in diameter) and particle concentrations (0.0001% to 10% wt./vol.) and bovine serum albumin (BSA) solutions with different concentrations (2% to 10%). The DLS system uses an avalanche photodiode (APD) based photon counting module (EG&G Model SPCM-250) and a digital correlator (Brookhaven Instrument, Model BI9000). The experiment duration is set at 30 seconds. The input laser power is adjusted to between 10 nW and 3 mW depending on the sample concentration and the particle size so that the average count rate is maintained around 200 Kcps. The computer performs a cumulant analysis routine to calculate average particle size and a CONTIN analysis routine to calculate particle size distribution. Both routines are commercially available as a part of the correlator package (Brookhaven Instrument).

In another preferred embodiment, a semiconductor laser (Toshiba TOLD9215) is used as the source of laser light.

In another preferred and portable embodiment, the data acquisition system is a Pentium based laptop computer with a docking station that houses a digital correlator (Brookhaven Instrument, Model BI9000).

Figure 3:
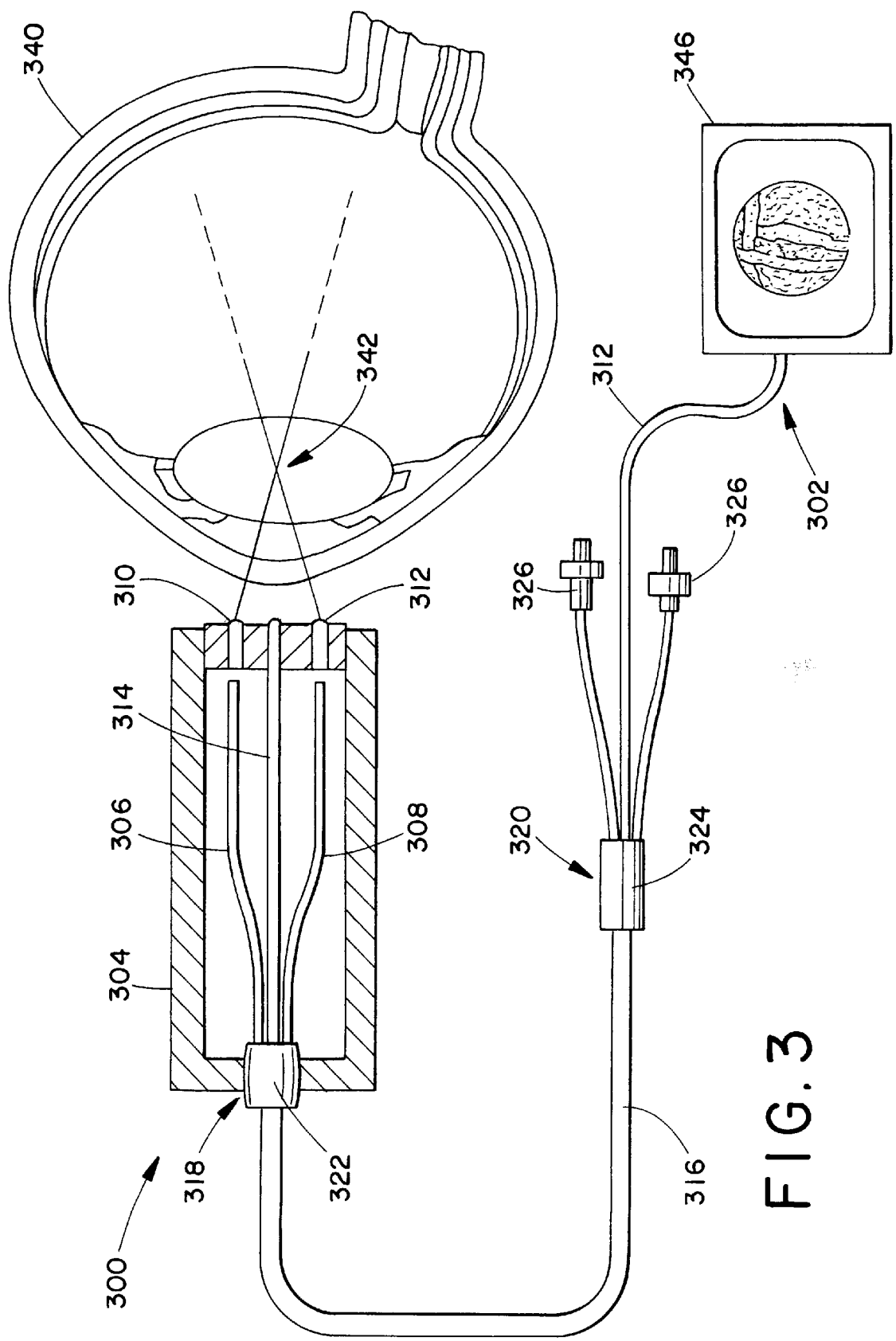
FIG. 3 illustrates in vivo use of another preferred DLS system of the present invention incorporating a miniaturized video microscope to study the dynamical characteristics of the macromolecules in the eye.

FIG. 3 illustrates in vivo use of another preferred embodiment of the present invention incorporating a miniaturized video microscope as a visual monitoring device. The DLS/video probe 300 is similar to the probe of FIG. 1 but provides video capability using a commerical video system 302. Probe body 304 houses transmitting optical fiber 306 and receiving optical fiber 308. Associated with these fibers are transmitting and receiving GRIN lenses 310, 312, respectively. The probe body also houses an image transmitting conduit 314 for real-time visual monitoring of a scattering volume or target. Flexible tubing 316 surrounds the optical fibers and the conduit. At the junctions 318, 320 of the flexible tubing and the optical fibers and conduit are small sections of Teflon tubing 322, 324. At ends of the transmitting and receiving optical fibers are FC/PC-type male connectors 326, 328 for easy mating with an associate laser and detector (not shown). The probe is positioned to examine an eye 340 using DLS and video. More particularly, the probe is positioned such that the penetration depth of the probe reaches a scattering volume 342 in the middle portion of eye lens 344. A DLS examination is performed using associated equipment described above. Simultaneously with the DLS experiment, the visual optical fiber permits real-time viewing of the scattering volume, lens, cornea or other portion of the eye. The desired image is displayed by the video system on video monitor 346.

The DLS/video probe may be used to study the dynamical characteristics of the macromolecules in the eye. Such a probe can also be applied with experiments in protein crystal growth, polymer induced flocculation and aggregation, complete eye diagnostics, and the synthesis of microporous materials.

The present invention may also incorporate other visual monitoring devices such as a low magnification fiberscope or high magnification video microscope. This capability is especially attractive in applications which require the precise positioning of the scattering volume or testing volume within the sample. An example of such an application is in early diagnosis of various eye diseases. Further, this embodiment may be used in many other applications such as protein crystal growth experiments in which the particles under study grow to a size beyond the range of DLS yet still need to be monitored by video.

In another embodiment, the visual monitoring system is detachable to allow different video imaging systems such as low magnification fiberscopes and high magnification videoscope to be advantageously used.

The probe is non-invasive and is conveniently positioned in front of the eye (cornea) without any physical contact with the eye. Laser light is launched from a laser diode through the probe and into the eye. In a preferred embodiment, the probe focuses visible light of 670 nm wavelength from a laser diode into a small scattering volume inside the eye. The scattered light signal is detected and collected using a highly sensitive avalanche photodiode (APD) detector.

To further detail the present invention, it is necessary to study the imaging principles of a lens, the Gaussian beam propagation through a lens, and generation of the minimum scattering volume.

1. Imaging principle of a lens

Figure 4:
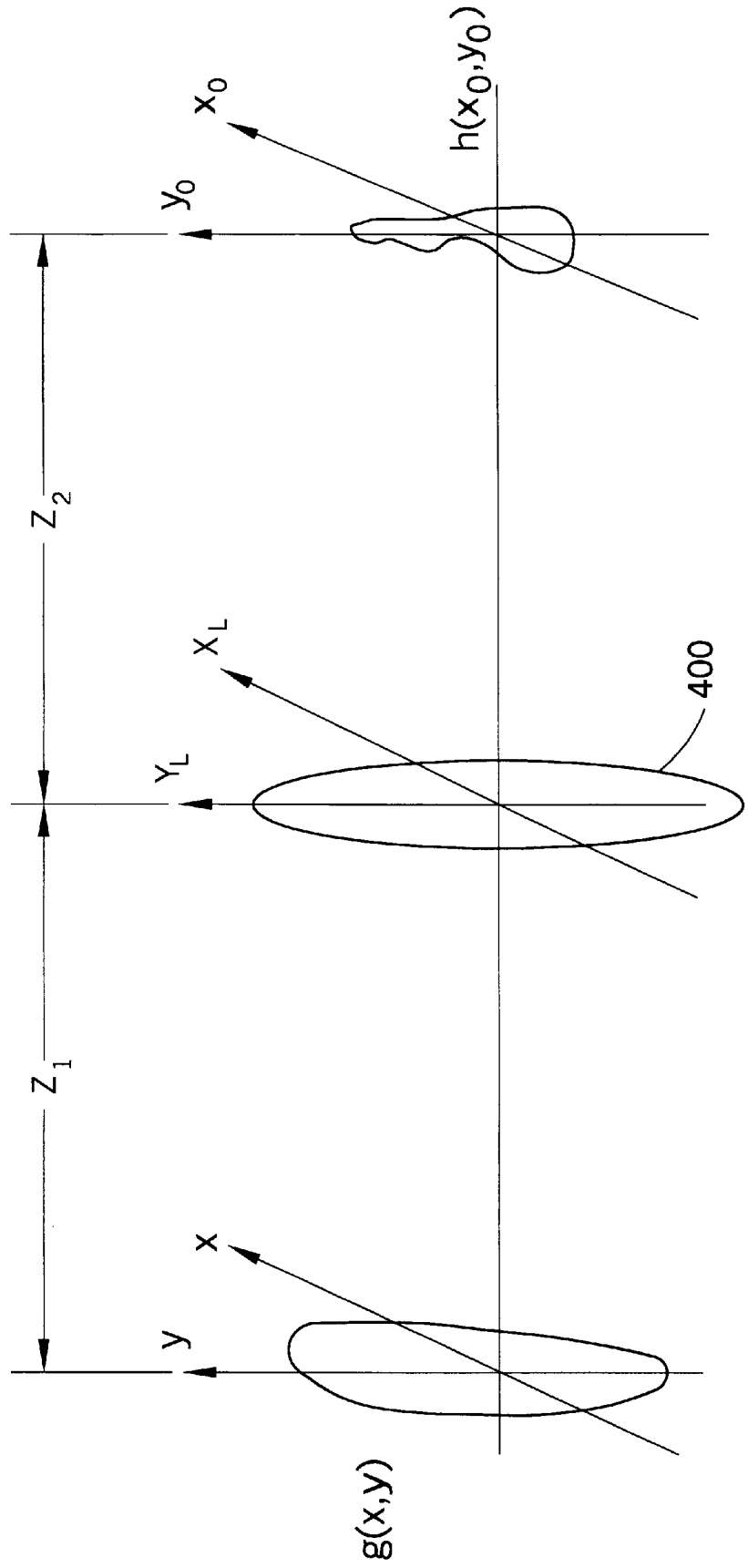
FIG. 4 is an optical diagram illustrating the relationship between the input and output optical fields of a lens in a probe of the present invention.

Referring to FIG. 4, suppose there is a lens 400 with focal length f and an input optical field g(x,y) at a distance $z_1$ from the lens on the left. Suppose it is of interest to measure the output field $h(x_o, y_o)$ at a distance $z_2$ away from the lens on the other side. Then, based on the theory of diffraction from the book by Guenther (Modern Optics, 1990), the output field $h(x_o, y_o)$ can be expressed as $$h(x_0, y_0) = \frac{-1}{\lambda^2 Rr} \exp[i2k(R+r)] \exp\left[-\frac{ik(x_0^2 + y_0^2)}{2r}\right] \quad (1)$$

$$\int\int\int\int f(x,y) \exp\left[-ik\frac{(X_L^2 + Y_L^2)}{2}\left(\frac{1}{R} + \frac{1}{r} - \frac{1}{f}\right)\right]$$

$$\exp\left[-ik\frac{(x^2 + y^2)}{2R}\right] \exp\left[ikX_L\left(\frac{x}{R} + \frac{x_0}{r}\right)\right]$$

$$\exp\left[ikY_L\left(\frac{y}{R} + \frac{y_0}{r}\right)\right] dx dy dX_L dY_L$$

If the distances $z_1$ and $z_2$ are set as the object and the image distances according to the Gaussian lens equation $$\frac{1}{z_1} + \frac{1}{z_2} = \frac{1}{f} \quad (2)$$

then the output field $h(x_o, y_o)$ will become:

$$h(x_0, y_0) = \quad (3)$$

$$-\frac{z_1}{z_2} \exp[i2k(z_1 + z_2)] \exp\left[ik\frac{(x_0^2 + y_0^2)}{2z_2^2}(z_1 + z_2)\right] g\left(-\frac{z_1}{z_2}x_0, -\frac{z_1}{z_2}y_0\right)$$

which, in essence, is the inverted and magnified image of the input field. The resulting output intensity distribution $I_h(x_o, y_o)$ is derived as $$I_h(x_0, y_0) = \frac{z_1^2}{z_2^2} I_g\left(-\frac{z_1}{z_2}x_0, -\frac{z_1}{z_2}y_0\right) \quad (4)$$

where $I_g(x,y)$ is the intensity of the input field g(x,y), and the ratio $z_2/z_1$ is the magnification factor.

2. Gaussian Beam Propagation through a Lens

Figure 5:
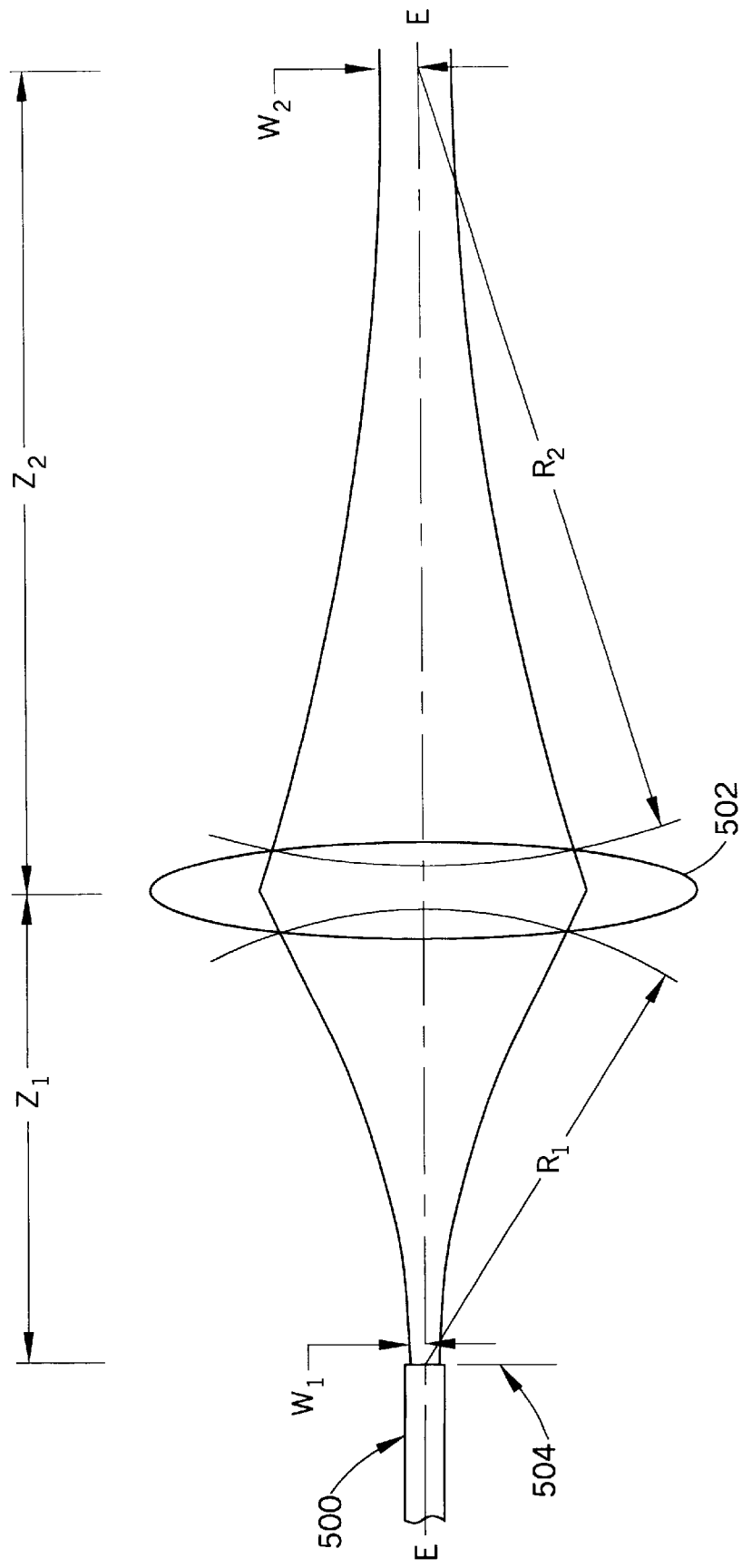
FIG. 5 is an optical diagram illustrating the Gaussian beam propagation through a lens of a probe of the present invention.

Referring to FIG. 5, suppose that a monomode optical fiber 500 is positioned against a thin lens 502 with the end face of the fiber 504 positioned a distance away from the lens on the optical axis E—E, and that a laser light is transmitted through the fiber. Then, a Gaussian beam is launched to a thin lens from the left side with minimum beam diameter $2\omega_1$ located on the optical axis of the lens at a distance $z_1$ away from the lens. The resulting field distribution $E_L(x,y)$ at the immediate left side of the lens will be, according to Kogelnik and Li [*Appl. Opt.*, 5, 1550 (1966)], $$E_L(x,y) = \frac{\omega_1}{\omega} \exp\left\{-j(kz_1 - \Phi) - (x^2 + y^2)\left(\frac{1}{\omega^2} + \frac{jk}{2R_1}\right)\right\}, \quad (5)$$

where $$\Phi = \arctan\left(\frac{\lambda z_1}{\pi \omega_1^2}\right) \quad (6)$$

and ω is the beam waist at the immediate left side of the lens, which is expressed as $$\omega = \omega_1 \sqrt{\left[1 + \left(\frac{\lambda z_1}{\pi \omega_1^2}\right)^2\right]} \quad (7)$$

Also, $R_1$ is the radius of curvature of the wave front at the immediate left side of the lens, and is expressed as $$R_1 = z_1\left[1 + \left(\frac{\pi\omega_1^2}{\lambda z_1}\right)^2\right] \quad (8)$$

If we assume that the distance $z_1$ is much larger than the minimum beam waist $\omega_1$, which is true in most cases (a few mm vs. a few $\mu$m), then we can simplify the equations (7) and (8) by approximation as $$\omega \cong \frac{\lambda z_1}{\pi\omega_1} \quad (9)$$

and $$R_1 \cong z_1 \quad (10)$$

Now, the field distribution at the immediate right side of the lens is related to the field distribution at the immediate left side of the lens by simple adding a phase term as $$E_R(x, y) = E_L(x, y)\exp\left(jk\frac{x^2 + y^2}{2f}\right) \quad (11)$$

$$= \frac{\omega_1}{\omega}\exp\left\{-j(kz_1 - \Phi) - (x^2 + y^2)\left(\frac{1}{\omega^2} + \frac{jk}{2R_1} - \frac{jk}{2f}\right)\right\}$$

The equation indicates that the resulting field at the immediate right side of the lens will be a converging Gaussian beam. As a result, we can denote the minimum beam waist and the radius of curvature of the resulting beam at the right side of the lens as $\omega_2$ and $R_2$, respectively, where $\omega_2$ is located on the optical axis of the lens at a distance $z_2$ away from the lens. Then, the term $$\frac{1}{2R_1} - \frac{1}{2f} \quad (12)$$

in equation (11) can be replaced with $\frac{1}{2}R_2$, and the relation between $R_1$ and $R_2$ can be set up as $$\frac{1}{R_1} + \frac{1}{R_2} = \frac{1}{f} \quad (13)$$

Applying the approximation from equation (10) for $R_1$ and the same approximation for $R_2$ would result in equation (2). This equation indicates that when a Gaussian beam is illuminated into a lens with its minimum beam waist placed at a certain distance $z_1$ away from the lens, another Gaussian beam would be produced at the other side of the lens as a result, and its minimum beam waist will be located at a distance $z_2$ away from the lens, where $z_1$ and $z_2$ are related by the Gaussian lens law as the object and image distances according to equation (2). Also, a further derivation and approximation will show that the minimum beam waist $\omega_2$ of the output beam is related to the minimum beam waist $\omega_1$ of the input beam by the magnification factor as $$\omega_2 = \frac{z_2}{z_1}\omega_1 \quad (14)$$

Figure 6:
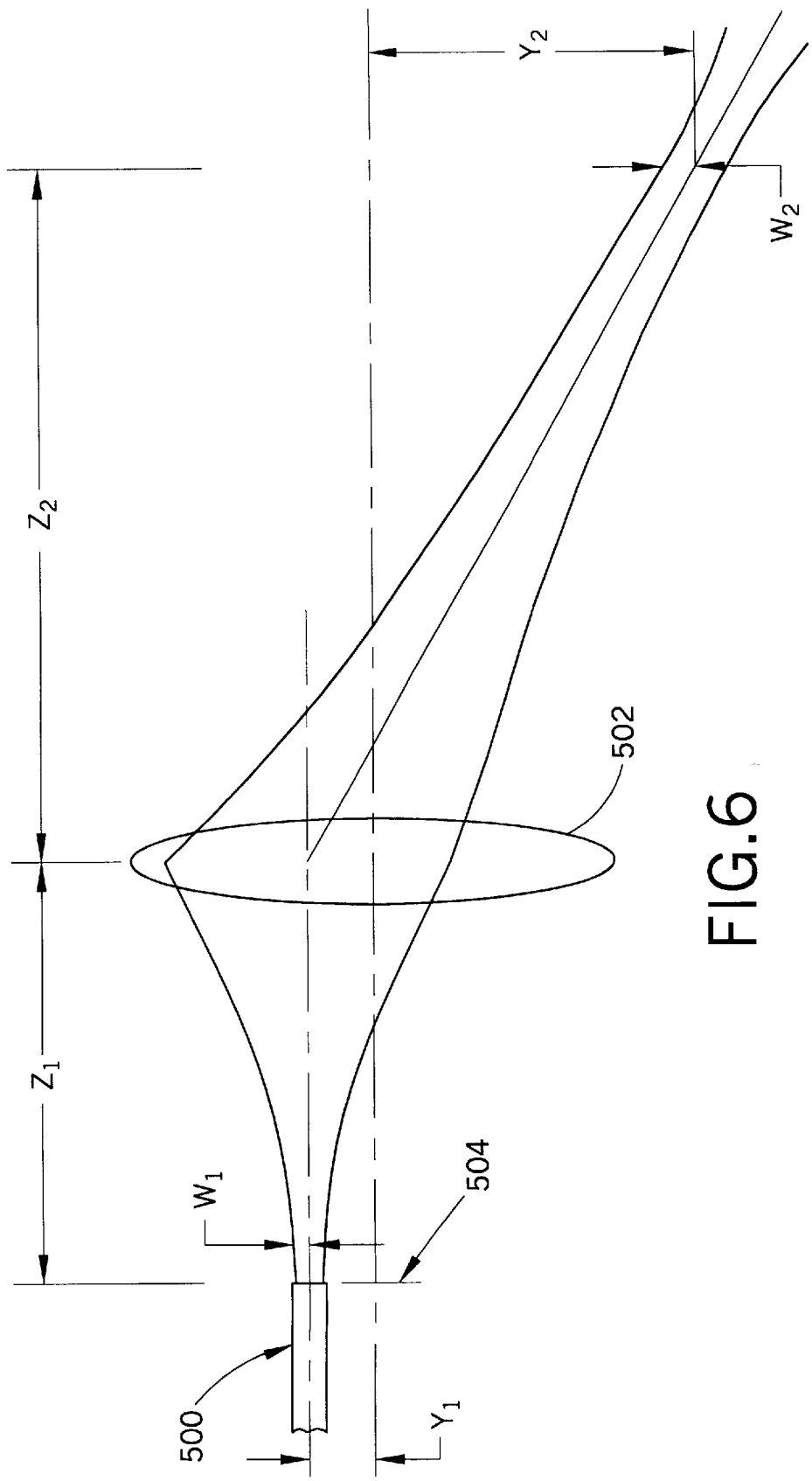
FIG. 6 is an optical diagram illustrating the Gaussian beam propagation of a monomode optical fiber positioned off the optical axis of a lens in a probe of the present invention.

Now, let us consider the case where the monomode optical fiber is positioned off the optical axis of the lens in y-axis, and therefore, the minimum beam waist $\omega_1$ of the input beam is located off the optical axis on the y-axis by $y_1$. Then, as shown in FIG. 6, the resulting output beam will propagate at an angle $\phi$ from the optical axis, which can be derived using geometric optics or ray matrix as $$\phi = \tan^{-1}\left(\frac{y_1}{z_1}\right) \quad (15)$$

Also, the resulting minimum beam waist of the output beam will be located at a distance $z_2$ away from the lens according to equation (14) and off the optical axis in the negative y direction by the distance $y_2$ where $$y_2 = z_2\tan(\phi) - y_1 \quad (16)$$

3. Generation of the Minimum Scattering Volume

Figure 7:
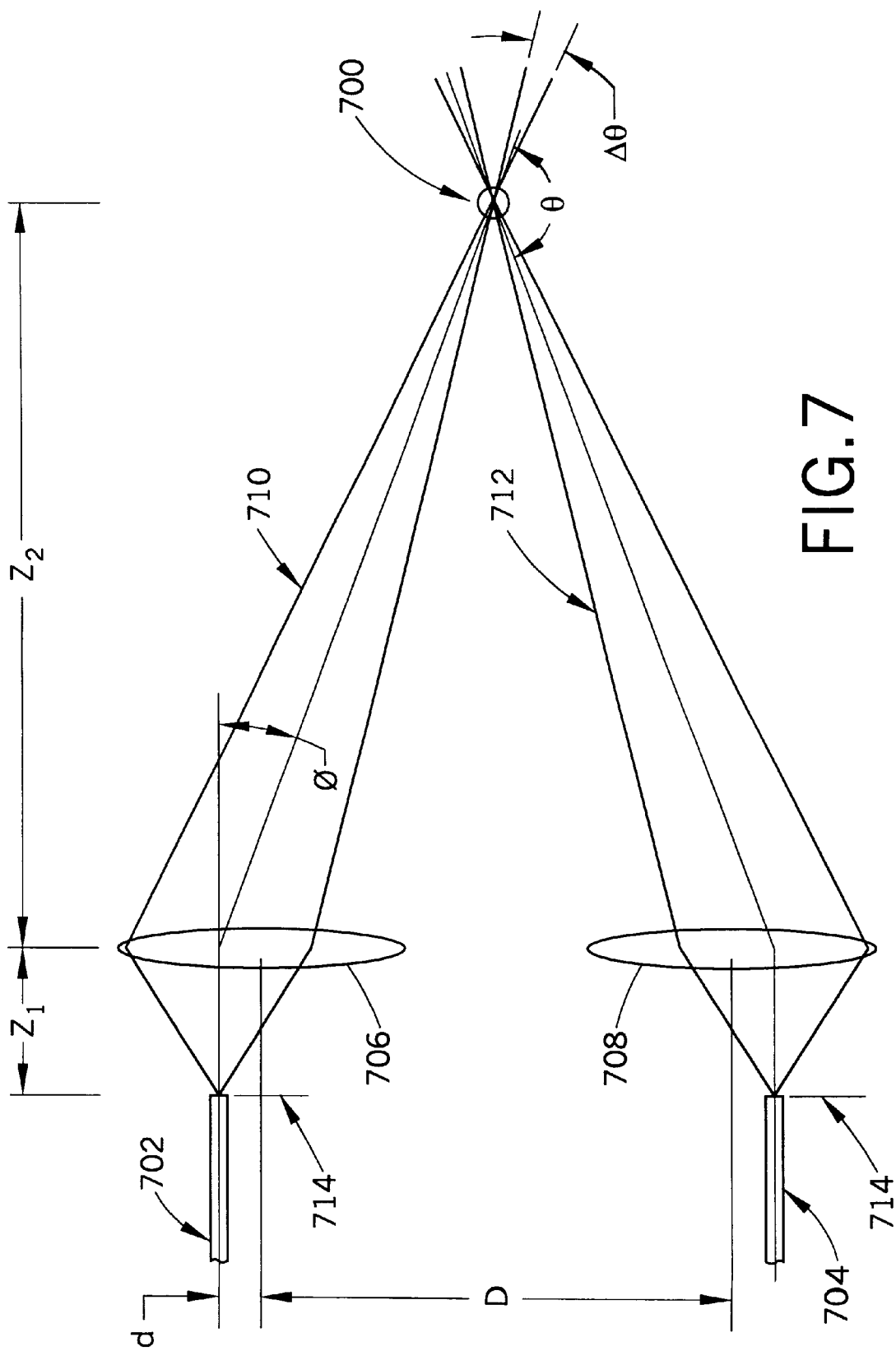
FIG. 7 is a lens diagram of a diagrammatic illustration of the optics of an imaging probe of the present invention.
Figure 8:
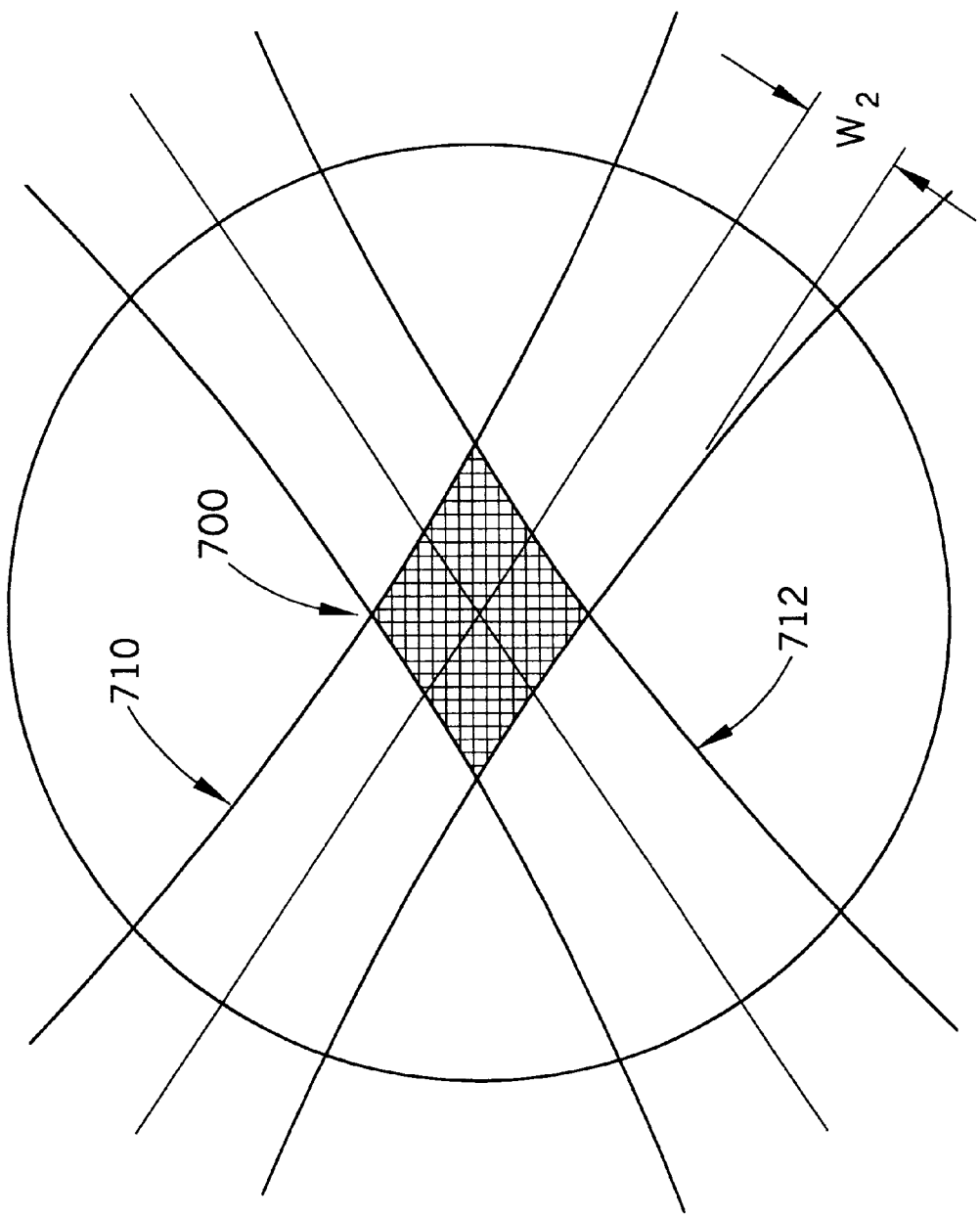
FIG. 8 is an enlarged diagram of the scattering volume shown in FIG. 7.

Referring to FIG. 7, the design objective of the present invention is to produce as small a scattering volume 700 as possible to optimize both the sensitivity and spatial coherence. Transmitting and receiving monomode optical fibers 702, 704 are combined with transmitting and receiving lenses 706, 708, respectively, to create transmitting and receiving beams 710, 712. An enlarged view of the overlap of the two beams, i.e., the scattering volume 700, is shown in FIG. 8. The fiber-lens combinations are in parallel according to the present invention. In each combination, an end face 714 of a fiber is positioned a distance $z_1$ away from its associated lens and a distance $y_1$ off the optical axis of the lens. The two fiber-lens combinations are mirror images of each other. The combinations are separated by a distance D (between the optical axes of the lenses). Given a pair of lenses of focal length f, a backscattering probe has penetration depth $Z_2$ and scattering angle $\theta$, which is related to the propagation angle of a Gaussian beam $\phi$ as $\theta = 180 - 2\phi$. Then, using the Gaussian lens law in equation (2), the distance $z_1$ between the end face of the monomode optical fiber and the lens is derived. The distance $y_1$ off the optical axis of the lens is derived using equation (15). The separation distance D between the optical axis of the two lenses is derived as $D = 2y_2$. Thus, an optimally dimensioned imaging probe is achieved having the smallest scattering volume possible given parameters of penetration depth, scattering angle, and focal length of the lenses.

Achieving the smallest scattering volume provides several notable advantages. First, the sensitivity of the system is maximized, and therefore, experiments on very dilute samples, solutions of very small particles, or solutions of very weakly scattering particles can be done easily. For instance, characterizing transparent tissues such as vitreous in the eye can be done with safe level of laser radiation. Second, the signal to noise ratio is maximized. As noted by Ford [*Measurement of Suspended Particles by Quasi-Elastic Light Scattering*, 31 (1983)], the smaller the scattering volume, the higher the spatial coherence. Also, the temporal incoherence of the light source would affect the scattered signal considerably less, since the pathlength difference of the scattered signal from different parts of the scattering volume is minimal. Lastly, the small scattering volume can be effectively used in studying highly concentrated suspensions without significant effect of multiple light scattering.

The small scattering volume has another advantage, temporal coherence. In DLS, it is assumed that the input laser light is a coherent light source, temporally and spatially. With the use of gas lasers such as He—Ne or Ar-Ion laser, the coherence length is long enough to validate this assumption. However, the assumption is no longer valid in DLS systems using semiconductor lasers. Semiconductor lasers have a shorter coherence length. This raises yet another problem when designing DLS systems. See Brown, "Optical Fiber Sensing Using Light Scattering Techniques", J. Phys. E: Sci. Instrum., vol. 20, pp. 1312–1320, 1987. The limited coherence length of light from a semiconductor laser can degrade the spatial coherence of the scattered light. This is because photons collected at the detector at a given time have traveled through different paths from the laser to the detector, and therefore, have different path lengths. If the maximum difference in the path length is much smaller than the coherence length of the input light, which is the case with the gas lasers, spatial coherence will not be affected. However, if the coherence length of the laser is short enough, which is the case with semiconductor lasers, spatial coherence can be degraded. Therefore, an objective of the present invention is minimize the difference in path length by minimize the scattering volume. This minimizes the negative effect that disparate path lengths have on temporal coherence.

Figure 9:
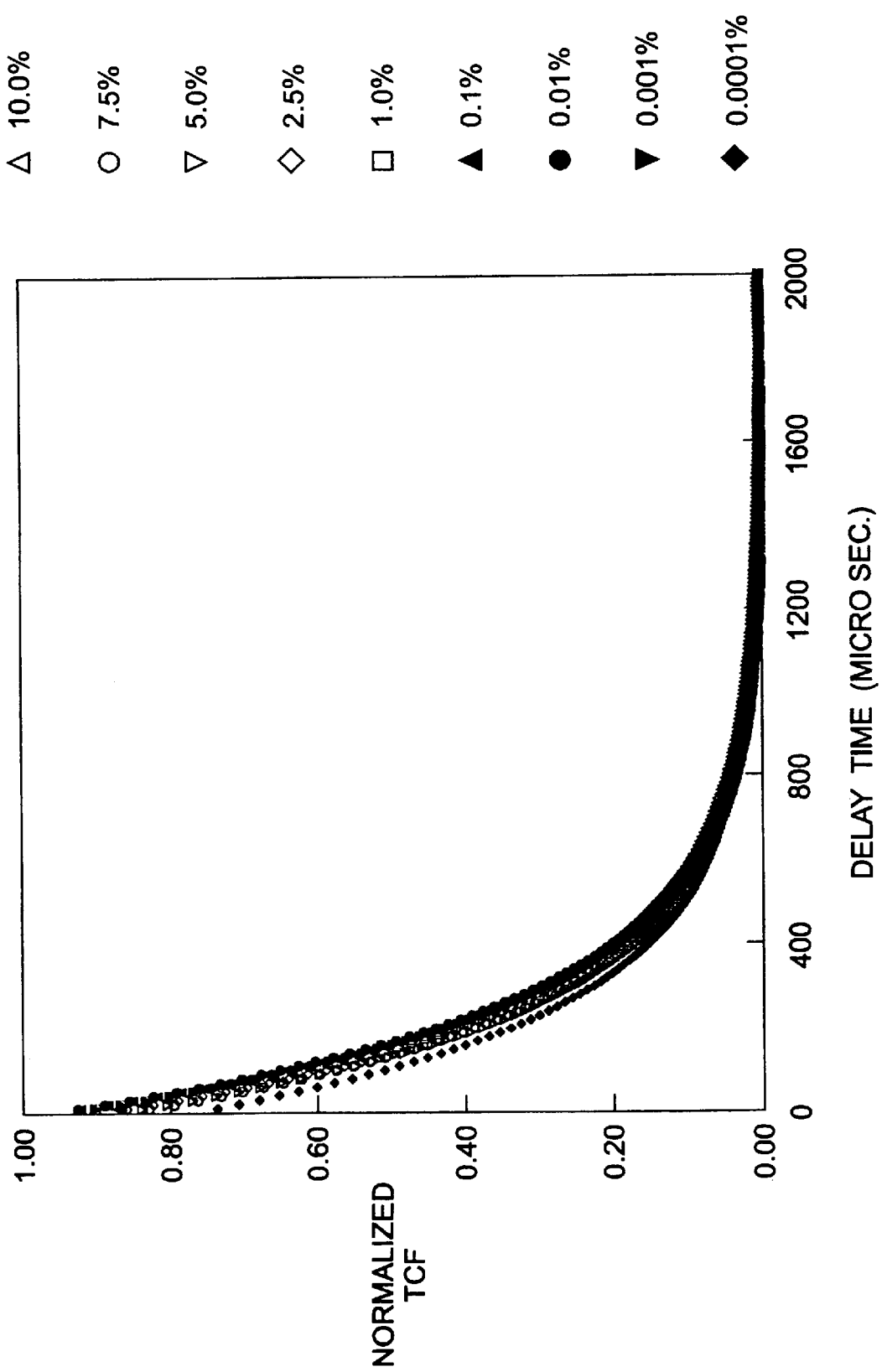
FIG. 9 is a graph of time correlation functions obtained from 157 nm polystyrene solutions at different concentrations using the present invention.

FIG. 9 shows the normalized time correlation functions obtained with 157 nm polystyrene particle solutions at different concentrations. As shown, the imaging probe is capable of producing very smooth TCFs throughout the entire range of concentrations without any indication of multiple light scattering. Also, it should be noted that the signal to noise ratio (also referred as spatial coherence or $\beta$) stays very high at around the 0.9 range.

Figure 10:
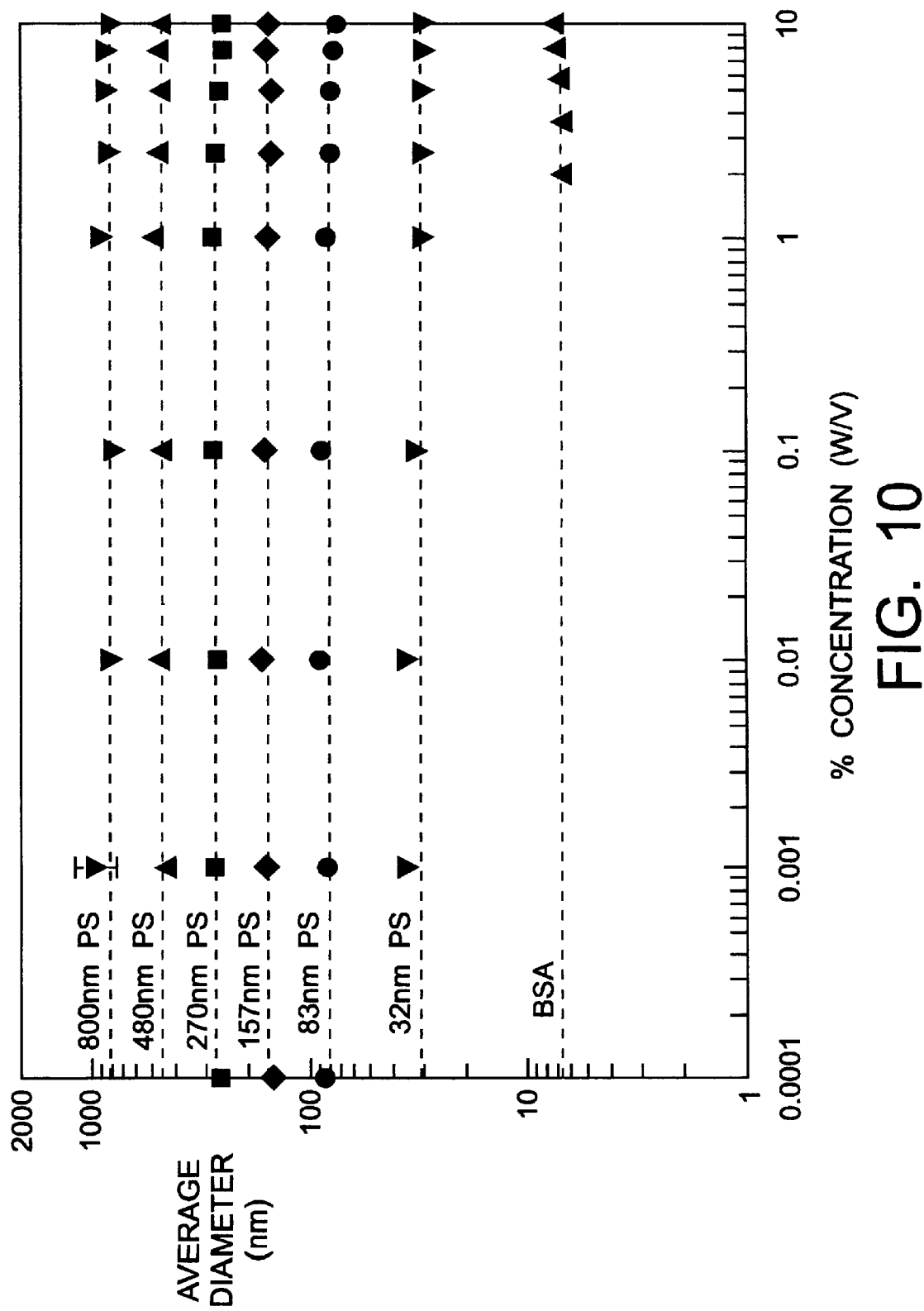
FIG. 10 is a graph of average particle size obtained from polystyrene solutions of different particle sizes and concentrations using the present invention.
Figure 11A:
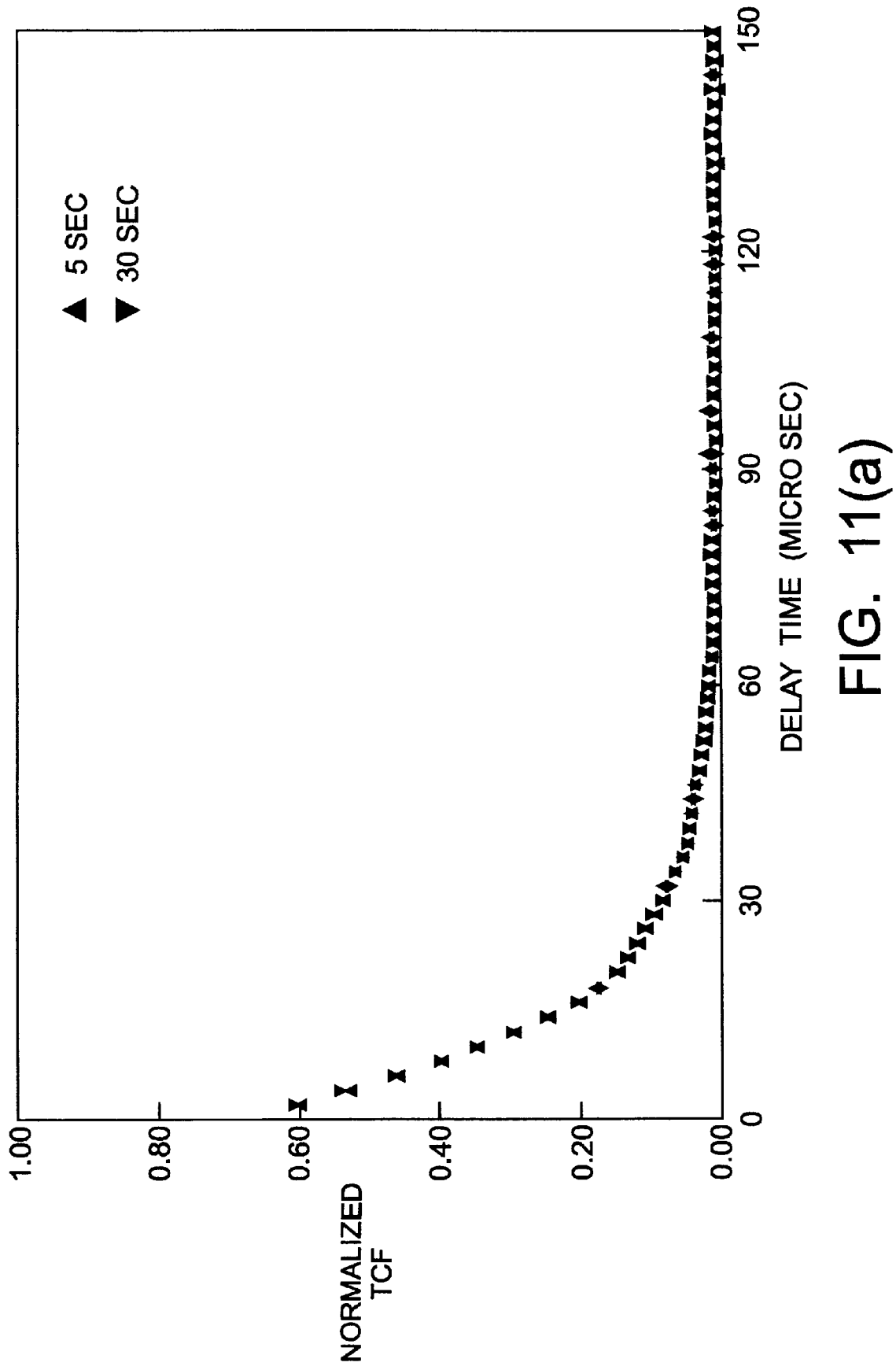
FIGS. 11(a) and 11(b) are graphs of a time correlation function and analyzed particle size distribution, respectively, obtained from 2% BSA solutions with different experimental durations using the present invention.
Figure 11B:
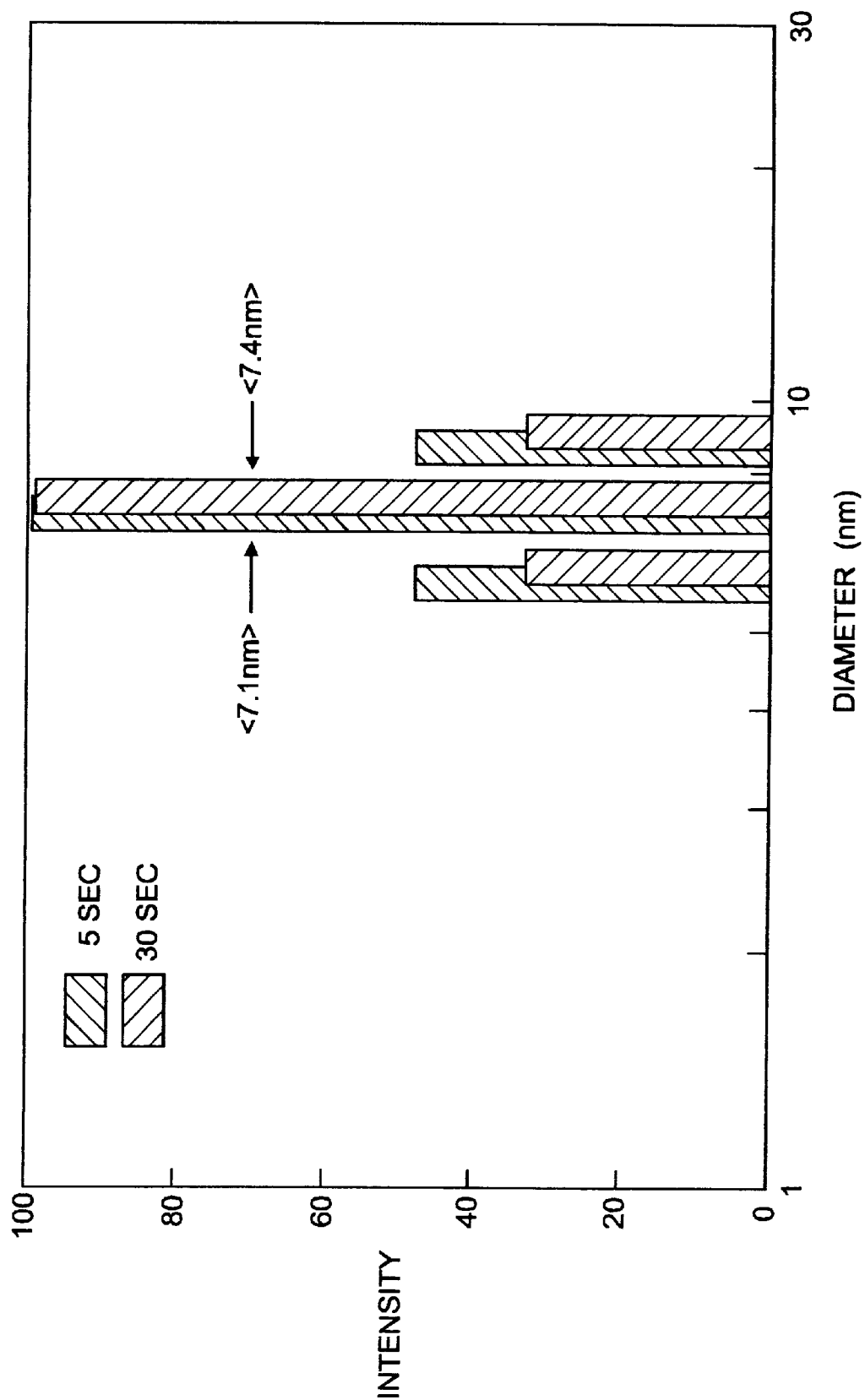

FIG. 10 shows the analyzed average particle size of the entire range of polystyrene and BSA solutions. From the graph, it is clear that the imaging probe can reliably and accurately determine the particle size from a very wide range of samples from a very dilute solution of very small particles (32 nm at 0.0001%) to a very highly concentrated suspension of large particles (800 nm at 10%). Accurate determinations in such a wide range of particle sizes and concentrations has never been reported, let alone with such a low level of laser power (10 nm to 3 mW). Also, in order to show the capability of accurately measuring the particle sizes even with a very short experiment duration, a 2% BSA solution is tried with two different experiment durations, 5 seconds and 30 seconds. The resulting TCF's and analyzed particle size distribution is presented in FIG. 11(a) and 11(b), respectively. The result shows almost identical TCF profiles and particle size distributions, confirming that the imaging probe is capable of accurately and reliably measuring the particle size with experiment duration as short as 5 seconds.

4. Applications

The present invention may be used in diverse DLS experiments such as early diagnosis of various eye diseases, monitoring of protein crystallization processes, study of polymer induced flocculation and aggregation phenomena, characterization of highly concentrated and interacting systems, synthesis of microporous material (zeolite crystal), and characterization of food protein. There are several publications and patents on the use of various DLS apparatus to detect several different eye diseases. For instance Bursell et al. (U.S. Pat. No. 4,836,207) patented a DLS apparatus to monitor cholesterol levels in the anterior chamber. Nakanishi et al. (U.S. Pat. No. 4,711,542 and U.S. Pat. No. 4,776,687), Ichihashi et al. (U.S. Pat. No. 4,854,693), Benedek (U.S. Pat. No. 4,957,113), Benedek et al. (U.S. Pat. No. 4,993,827), and Dhadwal et al. (U.S. Pat. No. 5,284,149) have their respective patents on using DLS to detect the early stage of cataract formation in eye lenses. Ricka et al. (Rev. Sci. Instrum., 67, 2615 (1996) and Swiss Pat. No. 23J0908H) teach a DLS system to characterize the vitreous of the eye. However, the present invention offers three significant advantages over the prior art.

First, the present invention is capable of characterizing the ocular tissues in all different parts of the eye including the anterior chamber, the lens, the vitreous, and the retina. The prior art detects diseases associated with only a certain part of the eye such as a cataract in the lens. The prior art fails to cover diseases associated with the other parts of the eye. The present invention is uniquely capable of performing complete ophthalmic diagnoses such as early detection of various diseases associated with all different parts of the eye (e.g., cholesterol, sugar, and inflammation level in the anterior chamber, cataract in the lens (both nuclear and peripheral cataracts), various diseases in the vitreous (vitreal-retinal detachment, vitreal liquefaction, diabetic retinopathy, etc.), and retinal detachment and degeneration).

Second, by moving the probe, the present invention uniquely scans 3-dimensionally the entire eye for any sign of diseases or abnormalities, effectively creating a complete image of the eye. Depending on the part of the eye that is scanned, the present invention can perform or generate a CORNEOGRAM scan for the anterior chamber, a CATARACTOGRAM scan for the lens, a VITREOGRAM scan for the vitreous, and a RETINOGRAM scan for the retina. Some publications dramatically illustrate the effectiveness of these scans. See, e.g., Eye World, Fall issue (1996).

Finally, the imaging probe of the present invention is a stand-alone device that incorporates monomode optical fiber and real time video imaging system in a single compact housing. Thus, it offers a great deal of flexibility for use in wide various arrangements. For instance, it can be used as a stand alone unit, can be attached to a conventional slit lamp apparatus using several different mechanisms including mounting on a H-ruby lens holder, or can be integrated into various ophthalmic instruments such as Scheimfluke Camera. Most prior art has been integrated as a part of the conventional slit lamp apparatus. This lacks the flexibility of being able to be used in various physical configurations. Many different experiments have been conducted on various live animals as well as excised eyes using various physical configurations, and several publications have resulted [Proc. SPIE, 2632, (1995), Proc. SPIE, 2673 (1996)].

The present invention is also used in monitoring various protein crystallization processes such as Lysozyme and Thaumatin using different methods such as temperature induced and vapor diffusion. Several publications have resulted from this work [Proc. SPIE, 2629 (1995), J. Crystal Growth, (1996)]. This work is significant in that the imaging probe is used for the first time to interrogate a sample having an extremely small volume (~30 $\mu$l) such as in a droplet configuration. Until now, it has been practically impossible to study the aggregation and crystallization process in a hanging droplet configuration using the prior art because of either a large scattering volume or a misalignment problem. The present invention is a major breakthrough in DLS offering the capability to study a sample with extremely small volume without the negative effects of reflection or misalignment.

In addition to DLS applications, the present invention can also be used for several other optical diagnostics techniques. They include but are not limited to, static light scattering, Brillouin scattering, Raman scattering, and Fluorescence spectroscopy. They share the common point with DLS in that an input light is required to illuminate a sample under study, and the desired information is obtained by detecting and studying the characteristics of an optical signal that is generated in reaction to the input light by the sample, whether it is a reflection, scattering, absorption, transmission, or fluorescence. Therefore, by utilizing different light sources, detectors, and analysis instruments, it is possible to perform different optical diagnostic techniques using the same fiber optic imaging probe.

The invention has been described with reference to the preferred embodiment and additional embodiments. obviously, modifications and alterations will occur to others upon a reading and understanding of this specification. It is intended to include all such modifications and alterations in the scope of the invention.

Having thus described the invention, it is now claimed:

1. A dynamic light scattering apparatus for analyzing a scattering volume, the apparatus comprising:
    a probe body;
    an optical arrangement for transmitting coherent light to and receiving scattered light from a scattering volume, the optical arrangement having a first optical fiber and a first lens, the first optical fiber having a first optical fiber end face at a first end portion and a second optical fiber end face, the first optical fiber end face being secured to the probe body, the first lens being optically connected to the first optical fiber and located a first selected distance from the first optical end face to minimize the scattering volume, the lens being secured to the probe body.

2. The apparatus as defined in claim 1 wherein the optical arrangement includes:
    a transmitting optical arrangement for transmitting coherent light to the scattering volume, the transmitting optical arrangement including one of the first optical fiber and a second optical fiber, the second optical fiber having a first optical fiber end face at a first end portion and a second optical fiber end face, the first optical fiber end face of the second optical fiber being secured to the probe body; and
    a receiving optical arrangement for receiving scattered light from the scattering volume, the receiving optical arrangement including the other of the first optical fiber and the second optical fiber.

3. The apparatus as defined in claim 2 further comprising:
    a second lens optically connected to and located a second selected distance from the other of the first optical fiber end faces of the first and second optical fibers to minimize the scattering volume.

4. The apparatus as defined in claim 1 wherein the first end face of the first optical fiber is located at an image plane of the first lens relative to the scattering volume.

5. The apparatus as defined in claim 3 wherein the first and second selected distances are substantially equal.

6. The apparatus as defined in claim 1 wherein the first lens is a GRIN lens.

7. The apparatus as defined in claim 2 wherein the first end portions of the first and second optical fibers are substantially parallel to each other within the probe body.

8. The apparatus as defined in claim 1 wherein the first end portion of the first optical fiber is positioned off the optical axis of the first lens.

9. The apparatus as defined in claim 1 wherein the first optical fiber is a monomide optical fiber.

10. The apparatus as defined in claim 2 further comprising:
    a source of coherent light optically connected to the transmitting optical arrangement;
    a detector optically connected to the receiving optical arrangement;
    a correlator connected to the detector; and
    a computer for generating data characteristic of the scattering volume, the computer receiving data from the correlator.

11. The apparatus as defined in claim 10 wherein the detector is a photodiode.

12. The apparatus of claim 1 further comprising:
    a visual monitoring system attached to the probe body for viewing the scattering volume.

13. The apparatus of claim 1 wherein:
    the end face of the first optical fiber is positioned for a desired penetration depth $z_2$ a distance $z_1$ from the first lens having focal length f according to the Gaussian lens equation in order to minimize the scattering volume.

14. A fiber-optic imaging probe for determining a characteristic of a target, the apparatus comprising:
    a source of coherent light;
    a probe body;
    a transmitting lens secured to the probe body;
    a receiving lens secured to the probe body;
    a transmitting optical fiber for transmitting light to the target, the transmitting optical fiber having first and second end portions, the first end portion secured within the probe body such that it lies off the optical axis of the transmitting lens, the first end portion having an end face, the second end portion connected to the source of coherent light;
    a receiving optical fiber for collecting light from the target, the receiving optical fiber having first and second end portions, the first end portion secured substantially parallel to the first end portion of the transmitting optical fiber such that first end portion of the receiving optical fiber lies off the optical axis of the receiving lens, the first end portion of the receiving optical fiber having an end face secured to the probe body, the second end portion of the receiving optical fiber connected to detector.

15. The apparatus of claim 14 wherein one of the transmitting and receiving lenses is a GRIN lens.

16. The apparatus of claim 14 wherein one of the first end faces of the transmitting and receiving optical fibers is located at a selected distance from its associated lens such that the end face is at an image plane of the target.

17. The apparatus of claim 14 wherein one of the transmitting and receiving optical fibers is a monomode optical fiber.

18. A method for examining a scattering volume, the method comprising:
    (a) transmitting laser light non linearly from a first optical fiber end face to the scattering volume, the laser light undergoing Gaussian propagation;
    (d) receiving back-scattered laser light nonlinearly from the scattering volume to an end face of a second optical fiber;
    (e) detecting the scattered light;
    (f) converting the detected light into data characteristic of the scattering volume.

19. A method according to claim 18 further comprising:
    (g) simultaneously with step (d), monitoring a physical image of the scattering volume.

20. A method according to claim 18 further comprising:
    producing a tightly focused scattering volume given a desired scattering angle and a desired penetration depth according to lens equations.

21. A dynamic light scattering (DLS) probe comprising:
    means to coherently transmit input light;
    means to coherently transmit scattered light;

means to produce a tightly focused scattering volume in a sample with desired scattering angle and penetration depth by utilizing the principles of imaging;

and means to visually monitor the sample in real time.

22. An apparatus according to claim 21 such that the means to coherently transmit input light comprises a monomode optical fiber and the means to coherently transmit scattered light comprises a monomode optical fiber.

23. An apparatus according to claim 21 such that the means to produce a tightly focused scattering volume with desired scattering angle and penetration depth by utilizing the principle of imaging comprises two lenses, each mated with a monomode fiber.

24. An apparatus according to claim 23 characterized in that the two combinations of monomode fiber and lens are housed together in one probe body and they positioned in parallel to each other and mirror imaged.

25. An apparatus according to claim 24 characterized in that for each fiber-lens combination, the end face of the monomode optical fiber is positioned off the optical axis of the lens and away from the lens such that the location of the scattering volume is related to the location of the end face of the monomode fiber and the focal length of the lens according to the Gaussian lens law.

26. An apparatus according to claim 21 such that the means to visually monitor the sample in real time comprises a detachable video microscope.

27. An apparatus according to claim 21 such that the means to visually monitor the sample in real time comprises a detachable fiberscope.

28. An apparatus according to claim 21 used for many diverse dynamic light scattering applications including but not limited to, early diagnosis of various eye diseases (cholesterol deposit and blood sugar level in anterior chamber, cataract in the lens, diabetic retinopathy and age related molecular change in the vitreous), monitoring protein crystallization process, study of polymer induced flocculation and aggregation, study of highly concentrated and interacting systems, characterization of food protein, monitoring of the synthesis of microporous material (zeolite crystal), and skin/tissue analysis.

29. An apparatus according to claim 21 to be used for other optical diagnostics techniques including static light scattering, Brillouin scattering, Raman scattering, laser Doppler velocimetry, fluorescence spectroscopy, and transmission and absorption spectroscopy.

* * * * *

UNITED STATES PATENT AND TRADEMARK OFFICE
CERTIFICATE OF CORRECTION

| | | |
|---|---|---|
| PATENT NO. | : 5,973,779 | Page 1 of 1 |
| APPLICATION NO. | : 08/828371 | |
| DATED | : October 26, 1999 | |
| INVENTOR(S) | : Rafat R. Ansari et al. | |

It is certified that error appears in the above-identified patent and that said Letters Patent is hereby corrected as shown below:

Col. 1 lines 3-4
Please insert the following:

--This invention was made with Government support under contract NCC 3-544 awarded by NASA. The Government has certain rights in the invention.--

Signed and Sealed this
Twenty-second Day of May, 2012

David J. Kappos
*Director of the United States Patent and Trademark Office*